United States Patent
Lombardi

(10) Patent No.: US 7,462,190 B2
(45) Date of Patent: Dec. 9, 2008

(54) STENT MATRIX

(75) Inventor: Sylvie Lombardi, Karlsruhe (DE)

(73) Assignee: ANGIOMED GmbH & Co. Medizintechnik KG, Karlsruhe (DE)

( * ) Notice: Subject to any disclaimer, the term of this patent is extended or adjusted under 35 U.S.C. 154(b) by 0 days.

(21) Appl. No.: 10/203,840

(22) PCT Filed: Feb. 13, 2001

(86) PCT No.: PCT/EP01/01562

§ 371 (c)(1),
(2), (4) Date: Nov. 15, 2002

(87) PCT Pub. No.: WO01/58384

PCT Pub. Date: Aug. 16, 2001

(65) Prior Publication Data
US 2003/0144725 A1    Jul. 31, 2003

(30) Foreign Application Priority Data
Feb. 14, 2000    (GB)    ................... 0003387.8

(51) Int. Cl.
*A61F 2/06*    (2006.01)

(52) U.S. Cl. .................... 623/1.13; 623/1.16; 623/1.19; 623/1.2; 623/1.34; 623/1.36

(58) Field of Classification Search ................ 623/1.15, 623/1.34, 1.36, 1.35, 1.17, 1.18, 1.19, 1.2, 623/1.13, 1.16
See application file for complete search history.

(56) References Cited

U.S. PATENT DOCUMENTS

| | | | |
|---|---|---|---|
| 5,061,275 A | 10/1991 | Wallstén et al. | |
| 5,246,445 A | 9/1993 | Yachia et al. | |
| 5,372,600 A | 12/1994 | Beyar et al. | |
| 5,693,086 A * | 12/1997 | Goicoechea et al. | 623/1.11 |
| 5,707,386 A | 1/1998 | Schnepp-Pesch et al. | |
| 5,749,880 A | 5/1998 | Banas et al. | |
| 5,800,526 A * | 9/1998 | Anderson et al. | 623/1.16 |
| 5,861,027 A * | 1/1999 | Trapp | 623/1.15 |
| 5,876,432 A * | 3/1999 | Lau et al. | 623/1.13 |
| 6,086,611 A * | 7/2000 | Duffy et al. | 623/1.35 |
| 6,174,329 B1* | 1/2001 | Callol et al. | 623/1.34 |
| 6,231,581 B1* | 5/2001 | Shank et al. | 606/157 |
| 6,334,871 B1* | 1/2002 | Dor et al. | 623/1.34 |
| 6,344,054 B1* | 2/2002 | Parodi | 623/1.13 |
| 6,368,345 B1* | 4/2002 | Dehdashtian et al. | 623/1.13 |
| 2001/0032010 A1* | 10/2001 | Sandock | 623/1.15 |

(Continued)

FOREIGN PATENT DOCUMENTS

DE    19516060 A1    11/1996

(Continued)

*Primary Examiner*—Thomas J Sweet

(57) ABSTRACT

To improve radiopacity in a stent, and to reduce trauma while improving stent anchoring, imported beads are mounted To stent precursor matrices. Specially attractive is to provide a ring of such beads on the end rings of stent structures featuring a cylindrical mid length section flanked by outwardly flared ends. The beads can be of the same or different material from that of the stent matrix. The beads can assist in drawing the stent into a sleeve of a delivery system. Beads can be used to reveal features of the stent away from an end ring, such as a fenestration in the cylinder. Beads can be fixed in a position mechanically or by welding.

34 Claims, 13 Drawing Sheets

U.S. PATENT DOCUMENTS

2003/0149475 A1 * 8/2003 Hyodoh et al. .............. 623/1.19

FOREIGN PATENT DOCUMENTS

| EP | 0 709 068 A2 | 5/1996 |
| EP | 0 938 879 A2 | 9/1999 |
| EP | 0 947 180 A2 | 10/1999 |
| EP | 0 948 945 A2 | 10/1999 |
| WO | WO 92/06734 | 4/1992 |
| WO | WO 94/12136 | 6/1994 |
| WO | WO 94/17754 | 8/1994 |
| WO | WO 97/16133 | 5/1997 |
| WO | WO 97/33534 * | 9/1997 |
| WO | WO 98/46168 | 10/1998 |
| WO | WO 00/45742 | 8/2000 |
| WO | WO 01/05331 A1 | 1/2001 |
| WO | WO 02/15820 A2 | 2/2002 |

* cited by examiner

Fig. 9
Fig. 10
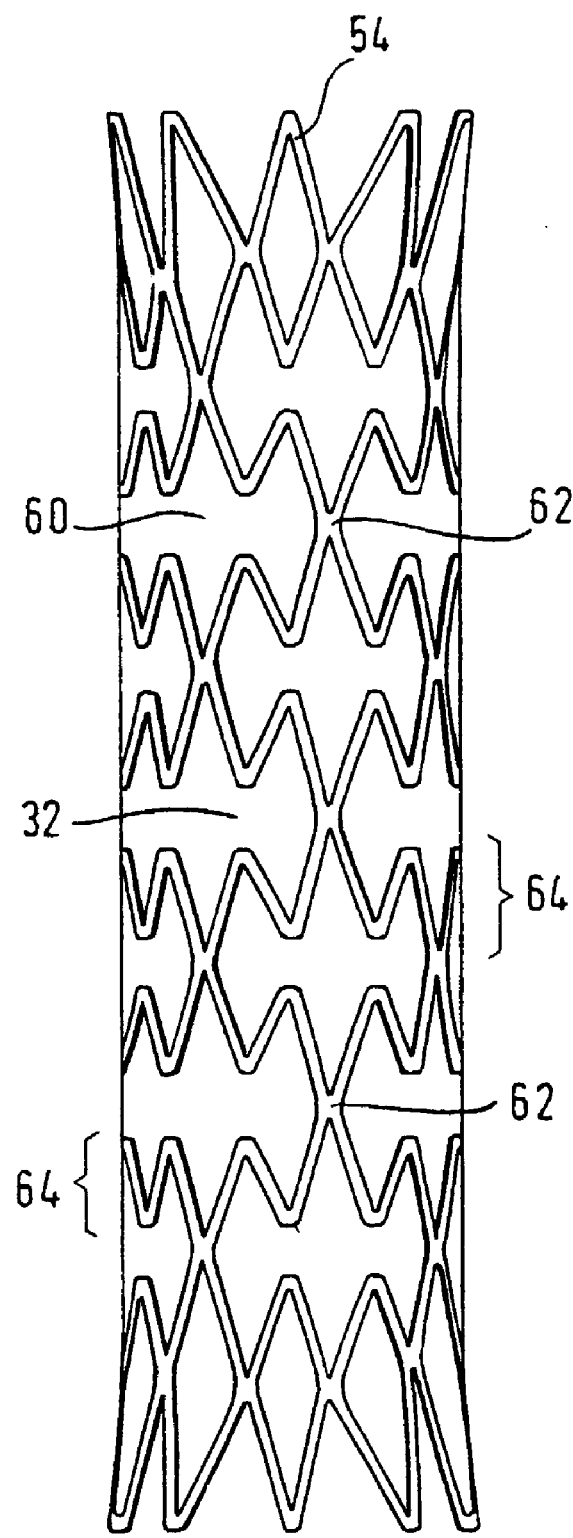
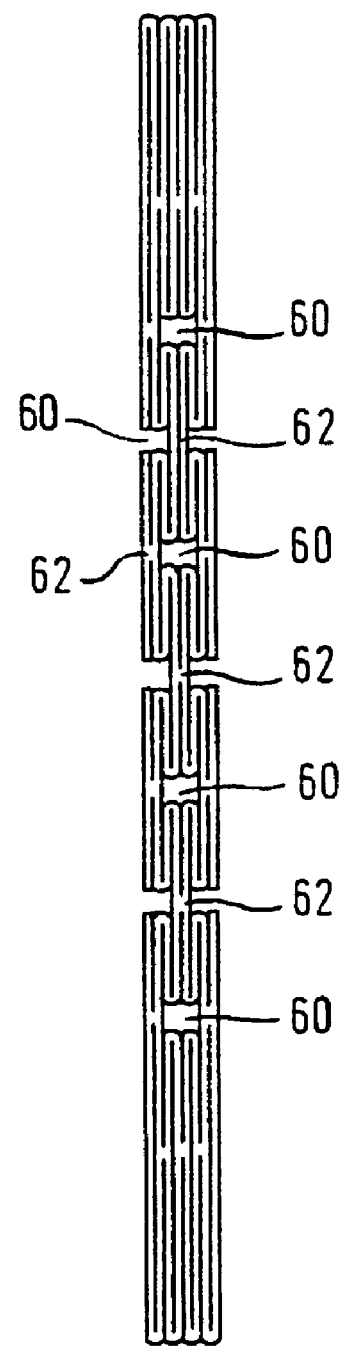

Fig. 13
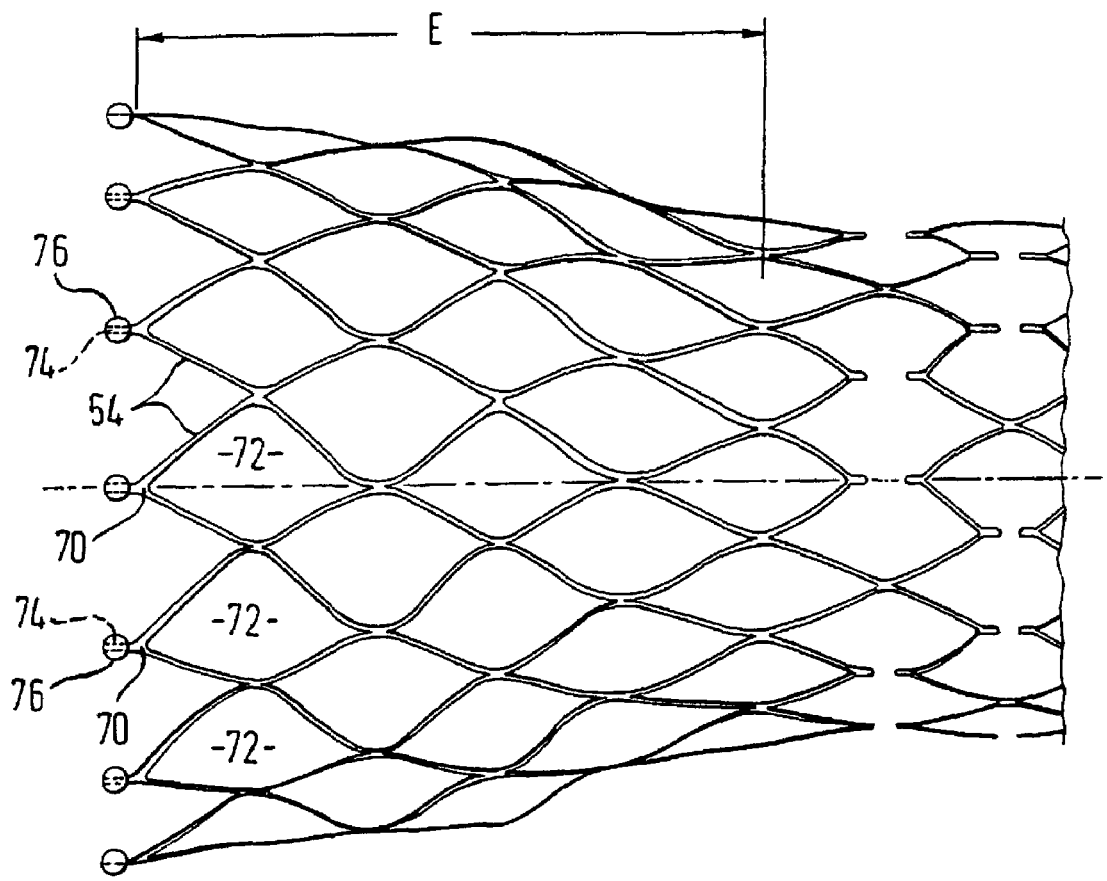
Fig. 14
Fig. 15
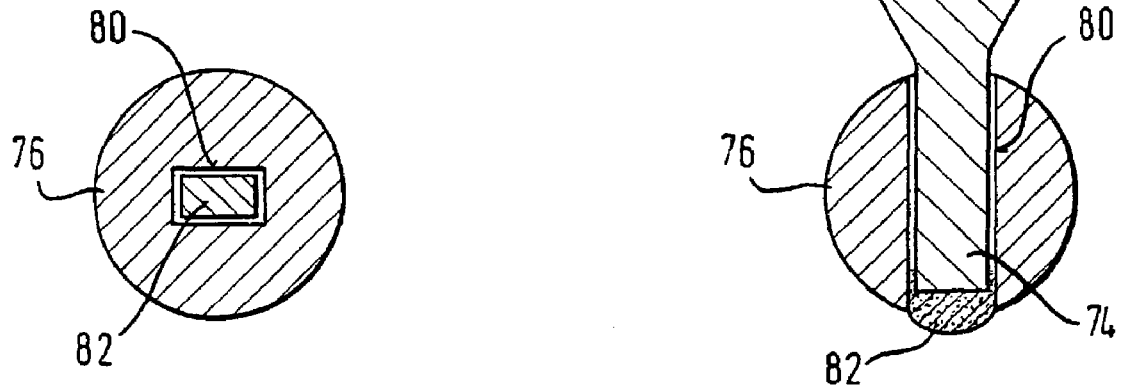

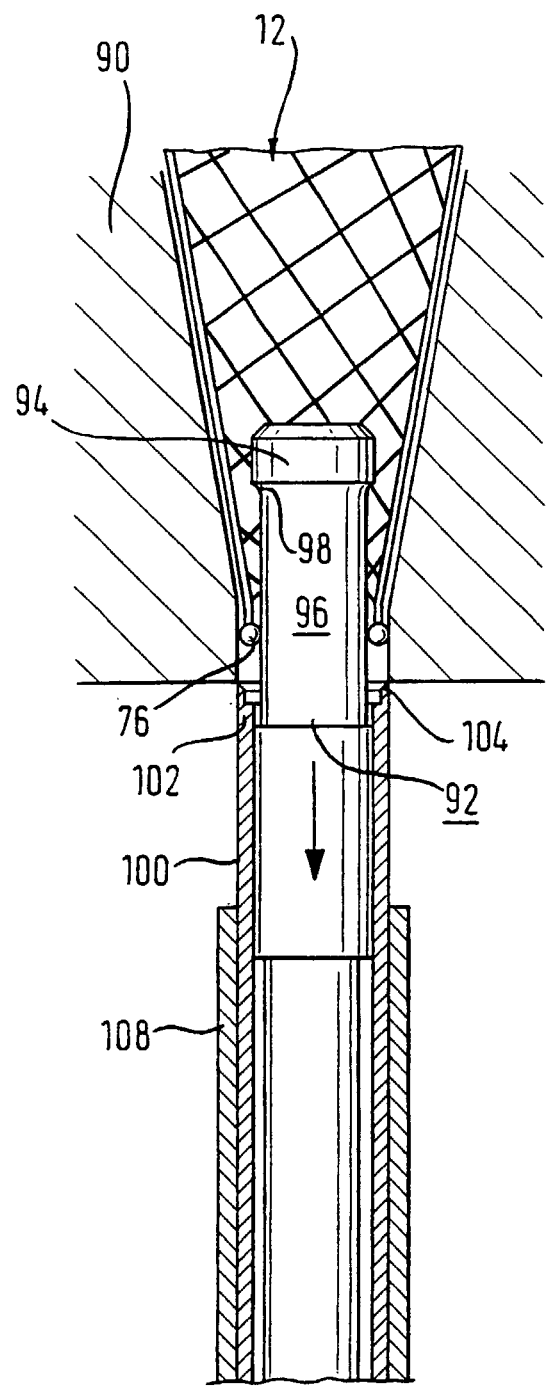
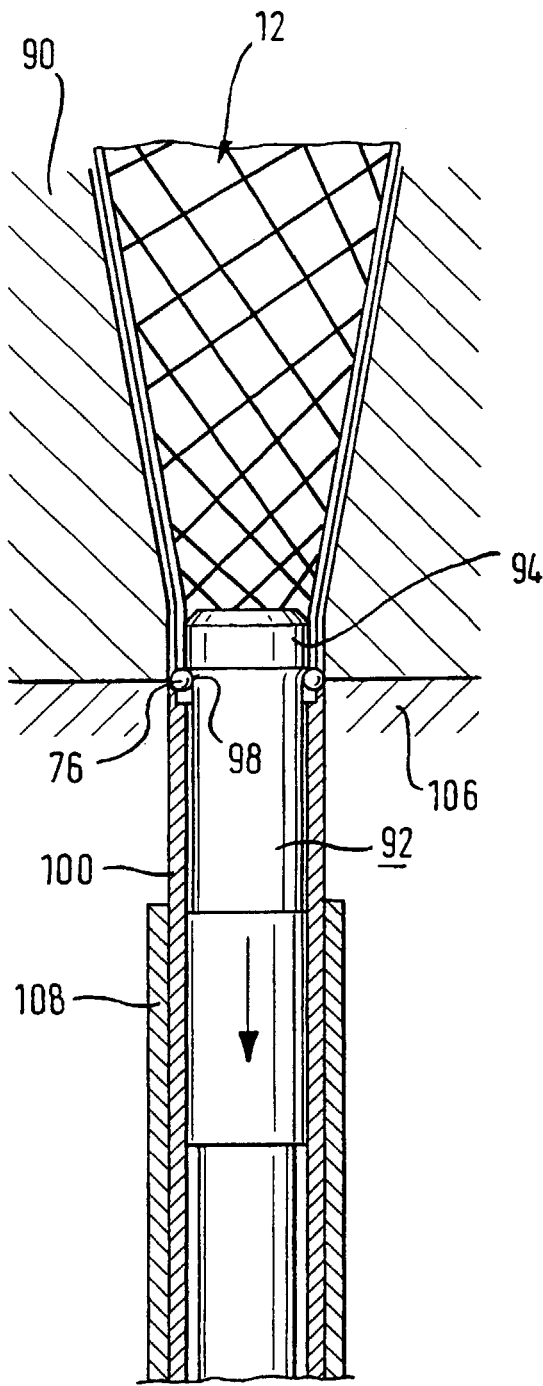
Fig. 16
Fig. 17

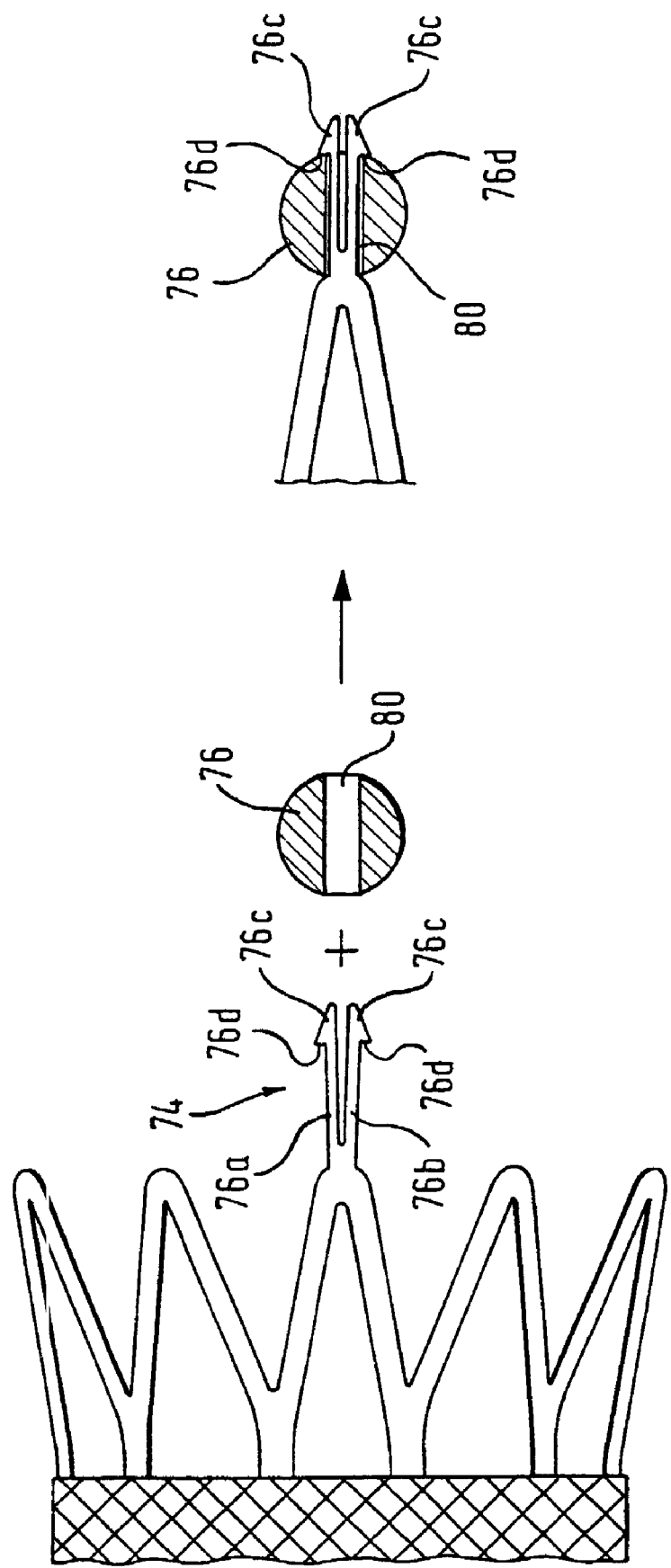

STENT MATRIX

FIELD OF THE INVENTION

This invention relates to an elongate stent matrix which defines a surface in a closed loop surrounding an elongate flow path, and which is capable of expansion during deployment in a bodily lumen, from a small diameter delivery configuration to a large diameter lumen wall-supporting configuration;

the matrix exhibiting a multiplicity of cells formed from struts, each of which cells has, at least in the delivery configuration, a length dimension along said flow path, a width dimension within said closed loop perpendicular to said flow path, and a thickness perpendicular to the length and width of the cell, with a first band of said cells at or near a first end of said matrix, and a further band of said cells at or near a second end of said matrix, opposite the first end;

the matrix further exhibiting a first ring which includes at least one free vertex.

Thus, this invention relates to prostheses to maintain patency of bodily lumens, and to precursors for such prostheses. The term "stent" is adopted, to signify such prostheses, because it is well-known and understood by those skilled in the art. Readers should appreciate that the term "stent" in this specification is to be understood to embrace all those prostheses which are useful for maintaining patency of a bodily lumen, whether, or not they are conventionally referred to, by those skilled in the art, as examples of stents.

It will also be understood that, in some applications, a stent matrix as described above is useful in itself whereas, in other applications, it requires some form of covering of a portion of its surface area, in order to be effective. Such a covered embodiment is sometimes referred to as a "stent graft" or as a "covered stent". The scope of the present invention includes such embodiments.

It is by now well-known that there are two prominent categories of stent, namely, self-expanding stents and stents which are expanded by inflation of a balloon within the flow passage of the stent, to cause plastic deformation of the metallic material making up the stent matrix, as it moves from its small diameter delivery configuration to its large diameter deployed configuration. Self-expanding stents are often made of a shape memory material, which normally is the nickel-titanium alloy known as NITINOL.

It is also well-known that stents are designed and built with particular applications in mind. Stents for maintaining the esophagus patent are of a different order of size from those constructed for maintaining open a coronary arterial lumen. The present invention is believed to be applicable to a wide range of stent applications, but one found particularly useful now is in the field of stents for the esophagus.

In designing stents for the esophagus, there are a number of tensions between opposing design objectives. First, there is a tension between a need to maintain a lumen diameter big enough to accommodate solid food as it is swallowed, and the need to avoid excessive trauma and pressure on the bodily tissue walls of the esophagus. Second, there is a tension between the need to anchor the stent securely in the esophagus so that the stent will not migrate along the length of the esophagus, and the need to avoid excessive trauma of the bodily tissue of the walls of the esophagus. Third, adequate radiopacity of the stent is needed, for tracking its location, but provision of sufficient bulk of dense material to achieve this objective tends to conflict with the overriding objective of achieving sufficient patency. To a greater or lesser extent these tensions can also be found in other stent applications, to which this invention also applies.

The present invention aims to provide improvements in the design compromises indicated immediately above.

BACKGROUND

For the disclosure of an esophageal stent see WO 92/06734. For a disclosure of stents made of Nitinol, see WO 94/17754. For a disclosure of stents covered in expanded PTFE, see for example US-A-5749880. WO 97 16133 discloses a stent fabricated by braiding of filaments. At each end of the stent is a ring of beads, created by fusing the material of the filaments of two intersecting stents of the braid.

Stents and similar endoluminal devices are currently used by medical practitioners to treat tubular body vessels or ducts that become so narrowed (stenosed) that flow of blood or other biological fluids is restricted. Such narrowing (stenosis) occurs, for example, as a result of the disease process known as arteriosclerosis. While stents are most often used to "prop open" blood vessels, they can also be used to reinforce collapsed or narrowed tubular structures in the respiratory system, the reproductive system, bile or liver ducts or any other tubular body structure including the esophagus. However, stents are generally mesh-like so that endothelial and other tissues can grow through the openings resulting in restenosis of the vessel.

Polytetrafluoroethylene (PTFE) has proven unusually advantageous as a material from which to fabricate blood vessel grafts or prostheses, tubular structures that can be used to replace damaged or diseased vessels. This is particularly because PTFE is extremely biocompatible causing little or no immunogenic reaction when placed within the human body. This is also because in its preferred form, expanded PTFE (ePTFE), the materials is light and porous and is readily colonized by living cells so that it becomes a permanent part of the body. In the process of making ePTFE of vascular graft grade the critical step is the expansion of PTFE into ePTFE. This expansion represents a controlled longitudinal stretching in which PTFE is stretched to several hundred percent of its original length.

Apart from use of stents within the circulatory system, stents have proven to be useful in dealing with various types of liver disease in which the main bile duct becomes scarred or otherwise blocked by neoplastic growths, etc. Such blockage prevents or retards flow of bile into the intestine and can result in serious liver damage. Because the liver is responsible for removing toxins from the blood stream, is the primary site for the breakdown of circulating blood cells and is also the source of vital blood clotting factors, blockage of the bile duct can lead to fatal complications. A popular type of stent for use in the biliary duct has been formed from a shape memory alloy (e.g. Nitinol) partially because such stents can be reduced to a very low profile and remain flexible for insertion through the sharp bend of the bile duct while being self-expandable and capable of exerting a constant radial force to the duct wall.

Cellular infiltration through stents also can be prevented by enclosing the stents with ePTFE. Early attempts to produce a stent covered by ePTFE focused around use of adhesives or physical attachment such as suturing. However, such methods are far from ideal and suturing, in particular, is very labour intensive. More recently methods have been developed for encapsulating a stent between two tubular ePTFE members whereby the ePTFE of one member touches and bonds with the ePTFE of the other member through the mesh opening in the stent. However, such a monolithically encapsulated stent may tend to be rather inflexible. Therefore, there is a need for a stent covered to prevent cellular infiltration and yet still flexible to ensure ease of insertion and deployment and to accommodate extreme anatomical curves.

SUMMARY

According to the present invention, a stent matrix is characterized by the fixing of an imported bead to the matrix, this bead having a thickness greater than the thickness which characterizes the struts of the matrix. The bead defines a female receiving portion, and the matrix includes a male extending portion which co-operates with the receiving formation. The greater thickness of the bead is useful for X-ray visualization and for secure attachment of the bead to the matrix. By "imported" is meant that the bead does not originate from within the matrix, but is brought in form a source other than the matrix itself.

For a stent matrix made of Nitinol, the struts of the matrix typically have a thickness up to about 0.3 mm and a width of within a range of from about 0.16 to about 0.20 mm. In the experimental work on esophageal stents so far conducted by Applicant, it has been found that a bead diameter in a range of from about 0.9 to about 1.1 mm is effective.

One basic structure of a self-expanding Nitinol stent is a cylinder of Nitinol material characterized by a multiplicity of short slits, in the longitudinal direction of the stent cylinder, these slits being arranged in successive rings of slits along the lengths of the stent, each ring being staggered circumferentially from the next adjacent rings, by regular intervals along the length of the stent. The slits of every second ring are co-linear. Then, when such a stent cylinder is expanded radially, a pattern of diamond-shaped openings appears. The length of the slits, and the circumferential spacings, are organized so that each diamond has a length direction parallel to the length of the stent cylinder, and a width direction around the circumference of the cylinder, when the stent is in its fully extended configuration.

In one useful embodiment of the present invention, each free vertex of each diamond-shaped cell at both ends of the stent cylinder has an axially-extending cantilever strut which serves as a male portion on which may be fitted one of the imported beads.

In another preferred embodiment of the present invention, every other such cantilever strut, at each end of the stent, is fitted with an imported bead.

In a specially preferred embodiment of the invention, stent matrixes which will receive a ring of beads at each end are modified from a strictly cylindrical configuration, in that the ring of cells at each end of the stent is worked upon, so as to incorporate a degree of outward flaring, relative to the generalized envelope of the stent between its two ends. The outward flaring tends to enhance the anchoring power of the stent ends in the bodily tissue of the lumen in which the stent has been installed, but the provision of the imported beads on the free vertices of each flared end will tend to ameliorate the degree of trauma to which the flared ends might otherwise subject the tissue into which they protrude.

In one preferred configuration for installation in the esophagus, the stent features ends which are outwardly flared by 15° relative to cylindrical end zones of the stent. Further, the esophageal stent features a mid-length zone which is cylindrical but of a diameter smaller than the flanking end zone cylinders, there being a stepless transition of diameter connecting each cylindrical end zone to the cylindrical mid-length zone. Further, the mid-length zone, but not the cylindrical end zones, is covered with a graft material, preferably expanded PTFE.

Nitinol stents can be formed from tubular material, or from initially flat material which, after laser cutting of the aforementioned slits, is then formed into a tube. Otherwise, stent matrixes can be etched from sheet material, either tubular or flat. For example, a stainless steel tube can be etched to make a stent which undergoes plastic deformation upon expansion by a balloon.

In a particularly preferred embodiment, the material of the imported beads is the same as that of the stent matrix, typically, stainless steel or Nitinol.

Alternatively, for the material of the imported beads, a material could be selected which has more or less the same electrochemical potential as that of the material of the stent matrix. For example, a Nitinol stent could be fitted with beads of Tantalum, which has almost the same electrochemical potential and greater radiopacity. Otherwise, each bead could be maintained electrically insulated from the matrix, as by an insulating layer for example a polymer.

In cases in which the bead and matrix material are the same they can be fixed to each other by welding. Otherwise, each bead could be fixed to the matrix by a mechanical engagement of co-operating surfaces, or by an intervening layer of adhesive, or by a tie layer of metal compatible with both the stent and the bead. In one preferred embodiment, each bead is spherical and defines a radially-extending recess which receives the cantilever strut to which the bead is fixed. The recess can be a bore through the entire bead. The radiopacity of the zone of the stent in which the beads are located is thereby enhanced. Further enhancements in radiopacity may be achieved by coating the bead in highly radiopaque material such as gold or tantalum.

In many stent applications, it is important that the delivery configuration of the stent exhibits as small a diameter as possible. Providing a relatively large diameter bead on every free vertex at each end of the stent will tent to limit the degree of compression of diameter which can be achieved at the beaded ends of the stent. Thus, in one specially preferred embodiment of the present invention, when an especially small diameter delivery configuration is needed, a bead is provided on a strut of every other free vertex at each end of the stent, rather than on every vertex. However, for delivery to the esophagus, a somewhat larger diameter delivery configuration, relative to the installed diameter configuration, is acceptable, which leaves room to place a bead on every one of the free vertexes at each end of the esophageal stent.

In applications where the objective of minimizing trauma dictates there should be a bead on every free vertex of the end ring of the stent, yet there is not enough room in the delivery configuration for so many spherical beads, it is contemplated to provide every free vertex around the end ring with a non-spherical bead having more or less the shape of a convex-ended cylinder with its long axis aligned with its female receiving portion.

In applications in which trauma is not a problem, beads can be positioned at will, depending on where enhanced radiopacity is needed. Thus, beads could be provided at points of importance along the length of the stent, or around the circumference of the stent. In one example, one or more beads could be placed near a fenestration in the stent wall, to be put into registry with a side branch of the lumen in which the stent length is being installed.

For a better understanding of the invention, and to show how the same may be put into effect, reference will now be made to the accompanying drawings.

BRIEF DESCRIPTION OF THE DRAWINGS

FIG. 9 shows an especially flexible stent design (the "Flexx" stent) preferred for use in the present invention; here the Flexx stent is shown in its expanded state;

FIG. 10 shows the flexible stent of FIG. 9 after it has been cut but before it has been expanded;

FIG. 13 is a view of a fragment at one end of the FIG. 9 stent, showing the subject matter of the present invention;

FIG. 14 is a diametral section through one of the beads in FIG. 13, in a plane tangential to the stent cylinder;

FIG. 15 is a diametral section through the FIG. 14 bead, in a plane transverse to a diametral plane of the stent, and the plane of FIG. 14;

FIG. 16 is a section through the diameter of the stent, showing a leading end of the stent entering a loading machine;

FIG. 17 is a section as in FIG. 16, showing the stent leading advanced from the FIG. 16 position; and FIG. 18 is a side view of a fragment of one end of the FIG. 1 stent and (in section) of a bead to fit on that fragment, as well as the bead fitted to the fragment.

DETAILED DESCRIPTION

The present invention may be used with covered or uncovered stents. For example, it may be used with a covered stent device that is virtually as flexible as an uncovered stent. Such flexibility is accomplished by covering a stent on a first surface while limited regions are covered on the opposite surface to ensure fixation of the first surface covering.

Figure 1:
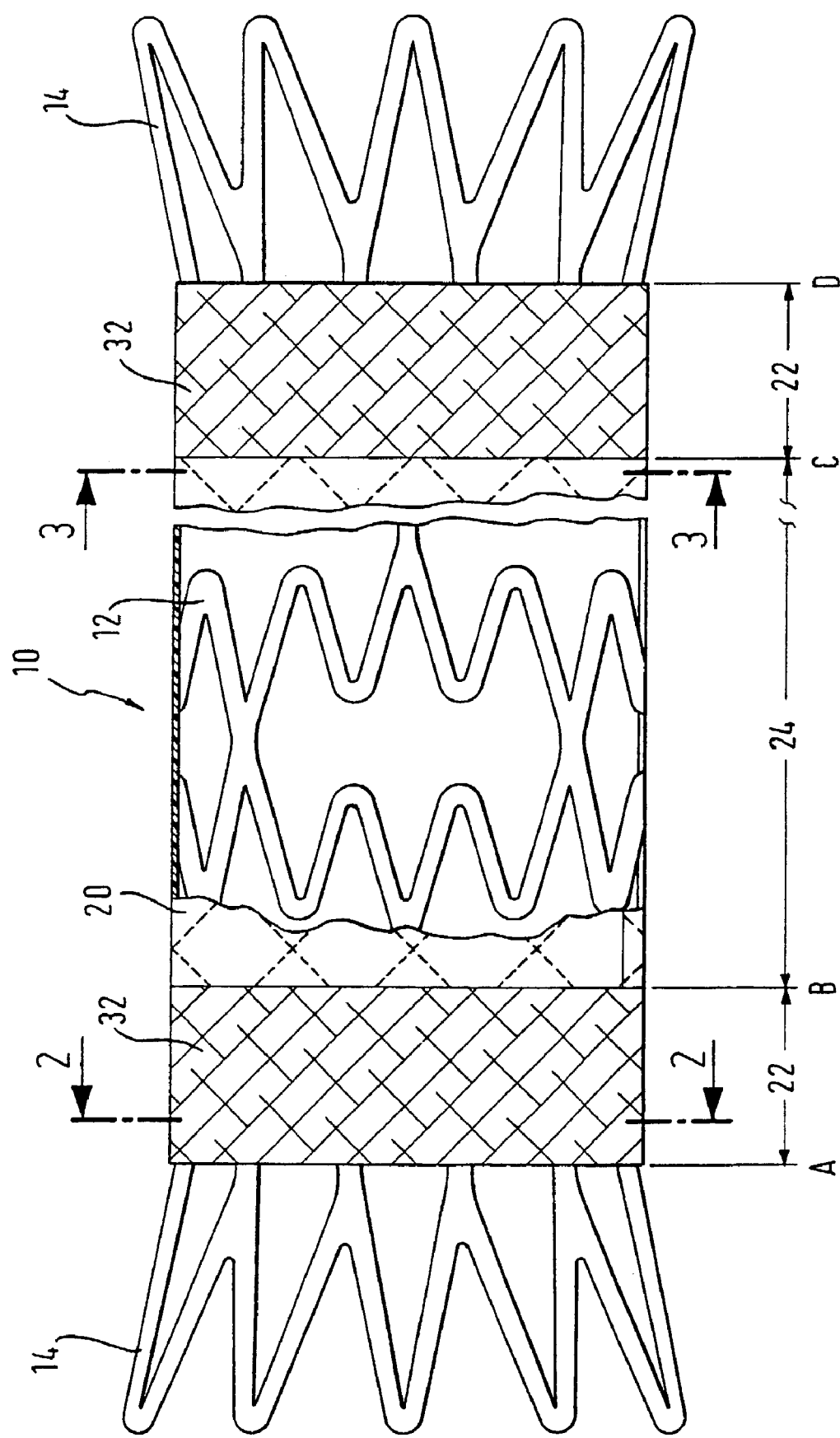
FIG. 1 is a perspective view of an esophageal stent graft.

Referring now to the drawings, in which like reference numbers represent similar or identical structures throughout, FIG. 1 illustrates a preferred embodiment of stent graft which is particularly well-adapted for incorporation of the present invention. A partially encapsulated stent-graft 10 is created by covering the abluminal surface of a stent 12 with a biocompatible barrier material that is able to seal fistulae and aneurysms and prevent or reduce tissue ingrowth from neointimal hyperplasia or tumour growth. In the preferred embodiment, the material used for this purpose is a tubular layer of expanded polytetrafluoroethylene (ePTFE) 20. the preferred ePTFE is one optimised for bond strength as described in U.S. Pat. No. 5,749,880. The stent 12 in the preferred embodiment is a shape memory alloy stent having enhanced flexibility, although stents of a variety of designs are usable with the current invention. Also, the stent 12 can be made out of any type of material besides shape memory alloy.

It is known to those of skill in the art that at a covering over at least one of the surfaces (luminal or abluminal) of a stent can prevent tissue ingrowth. Furthermore, the covering can be bonded to the stent to prevent it from coming detached and perhaps forming a blockage in the vessel. Although ePTFE has numerous favourable properties, it is relatively difficult to attach it to a stent. Mechanical fasteners such as sutures have the disadvantage of interrupting the integrity of the ePTFE sheet so that leaking can occur. Although ePTFE does not adhere well to a stent, it can be made to bond to itself. Therefore, one effective method of affixing the ePTFE cover is to place ePTFE covers in contact with both the abluminal and luminal surfaces of the stent so that one ePTFE covering can bond to the other where the ePTFE coverings touch through opening in the stent. The drawback with this approach is that the structural members of the stent are tightly surrounded and held by ePTFE. When the stent bends or expands, the stent structural members must move relative to each other. This movement is resisted by the tightly adhering ePTFE (or other covering material).

Movement of the stent members relative to each other is facilitated by limiting the region of the stent in which the structural members are surrounded (encapsulated) by ePTFE. In a preferred embodiment the regions of encapsulation, which ensure attachment of the covering to the stent, are limited to areas near the ends of the device but spaced from those ends. For a relatively short device these end-encapsulated regions are more than adequate to afford attachment of the covering. If necessary one or more additional regions of encapsulation could be added along the length of the device if it is found necessary for stability of the covering. Clearly, the greater percentage of length of the device that is fully encapsulated, the more the flexibility of the overall structure will be impeded. The ends are left uncovered, and are flared outwardly. This helps to prevent unwanted axial migration of the stent in the lumen. In other words, the flared end helps to anchor the stent in the walls of the lumen.

An additional advantage of the limited encapsulation is the possibility of enhanced healing. It is known that living cells will infiltrate sufficiently porous ePTFE and the microcapillaries may form within and across the ePTFE wall so that a living intima is formed along the luminal surface. Where two layers of ePTFE surround the stent, it may be significantly more difficult for cellular infiltration across the wall to occur. Although the figures show the continuous covering placed on the abluminal surface of the device, the illustrated embodiment also lends itself to placement of the continuous covering on the luminal surface. The configuration choice may depend on the precise application of the device. In some palliations, for example, large vessels having a high rate of blood flow, placing the covering on the luminal surface may result in advantageous lamellar flow of blood, that is to say, blood flow without significant turbulence. There is some evidence that contact of the blood with a metal stent may result in local, limited thrombosis. While this may be detrimental, there is also some evidence that some limited thrombosis results in enhanced healing. An advantage of using a full luminal covering could be improved anchoring of the device within the duct or vessel afforded by interactions between the bare abluminal stent and the duct or vessel wall. Therefore, the optimal configuration will have to be empirically determined in many cases.

In the illustrated design (FIG. 1) the extremities 14 of the stent 12 are left completely uncovered and flare outward to facilitate anchoring of the stent within the vessel following expansion of the stent in situ. It will be apparent that this flared region is a feature of this particular embodiment and is not a required element of the instant invention. The luminal surface of the stent 12 is covered at ends 22 defined between points A and B and points C and D in FIG. 1, but is left uncovered in mid-section 24 defined between points B and C. By leaving the mid-section 24 uncovered, the stent has increased flexibility as well as reduced profile when compressed. The material used to cover the ends 22 on the luminal surface of stent 12 is generally the same material that is used to cover the abluminal surface, and in FIG. 1 this material is ePTFE 30 (see FIG. 2), though any other suitable biocompatible material could be used in the present invention.

Again, it is important to note that while the continuous tubular layer of ePTFE 20 is shown on the abluminal surface of FIG. 1, is it possible, and advantageous in some cases, to place a tubular layer of ePTFE on the luminal surface, while placing limited rings of ePTFE only on the abluminal surfaces at the ends of the device. Distances A-B and C-D in FIG. 1 can be lesser or greater, depending on the need for flexibility in the particular application. Moreover, there can be any number of encapsulated region(s) and these region(s) can be located in different areas of the stent. Also, while the preferred embodiments use encapsulated regions that extend completely around a circumference of the device (e.g. rings of material) as indicated by region 32 in FIG. 1, there is no reason that discontinuous regions of encapsulation cannot be used. Attaching discrete pieces of strips of ePTFE to a mandrel before the stent is placed on the mandrel can be used to form such discontinuous regions. The size, shape and pattern formed by regions 32 can be selected to enhance flexibility, etc. This allows different regions of the device to exhibit different properties of flexibility, etc.

One the appropriate ePTFE covering is placed onto the luminal and abluminal surfaces, the ends 22 of the stent graft 10 are encapsulated by connecting or bonding the luminal covering to the abluminal covering. Encapsulation can be accomplished by a number of methods including sintering (e.g. heating), suturing, ultrasonically welding, stapling and adhesive bonding. In the preferred embodiment, the stent-graft 10 is subjected to heat and pressure to laminate (bond) the tubular ePTFE layer 20 on the abluminal surface to the two rings of ePTFE 30 (FIG. 2) on the luminal surface.

Figure 2:
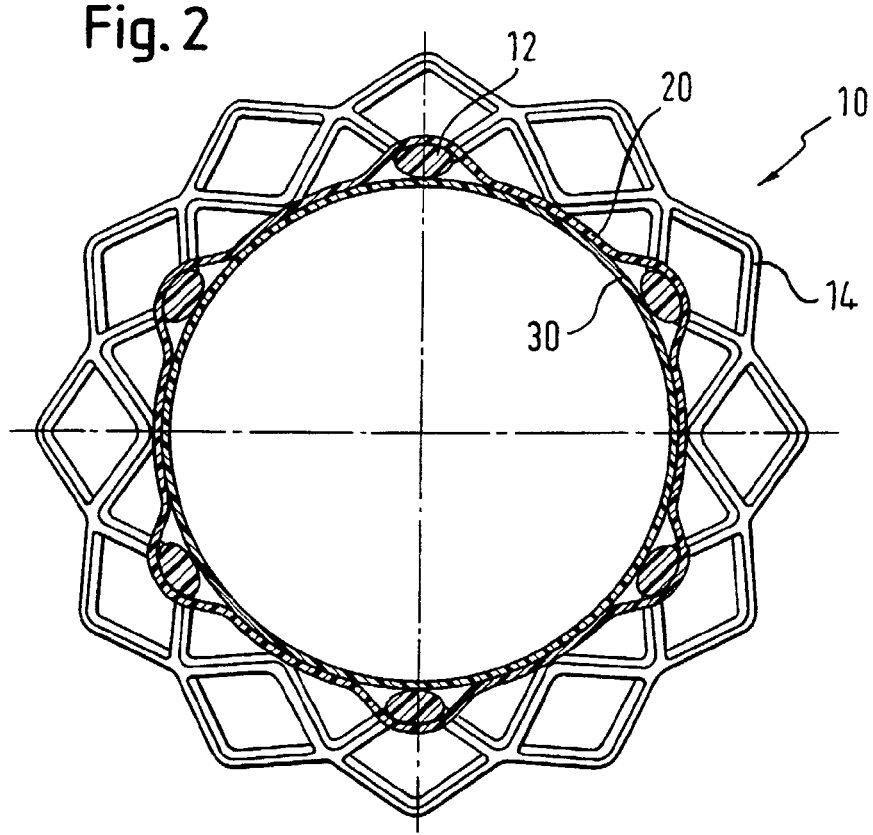
FIG. 2 is a cross-sectional view along the line 2-2.
Figure 3:
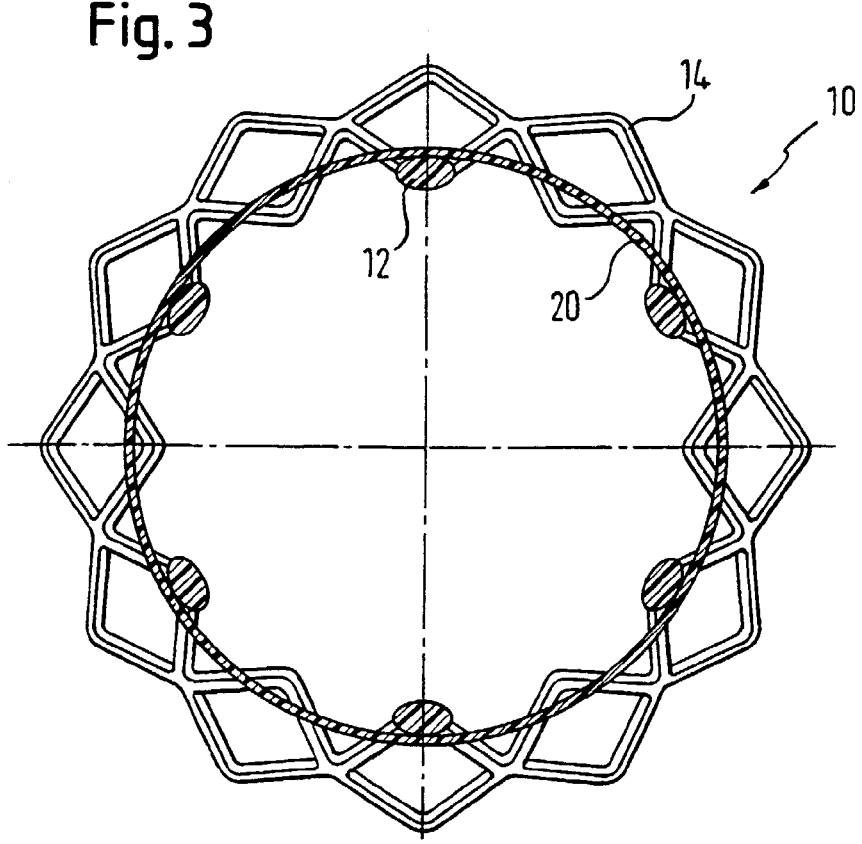
FIG. 3 is a cross-sectional view along the line 3-3.
Figure 7:
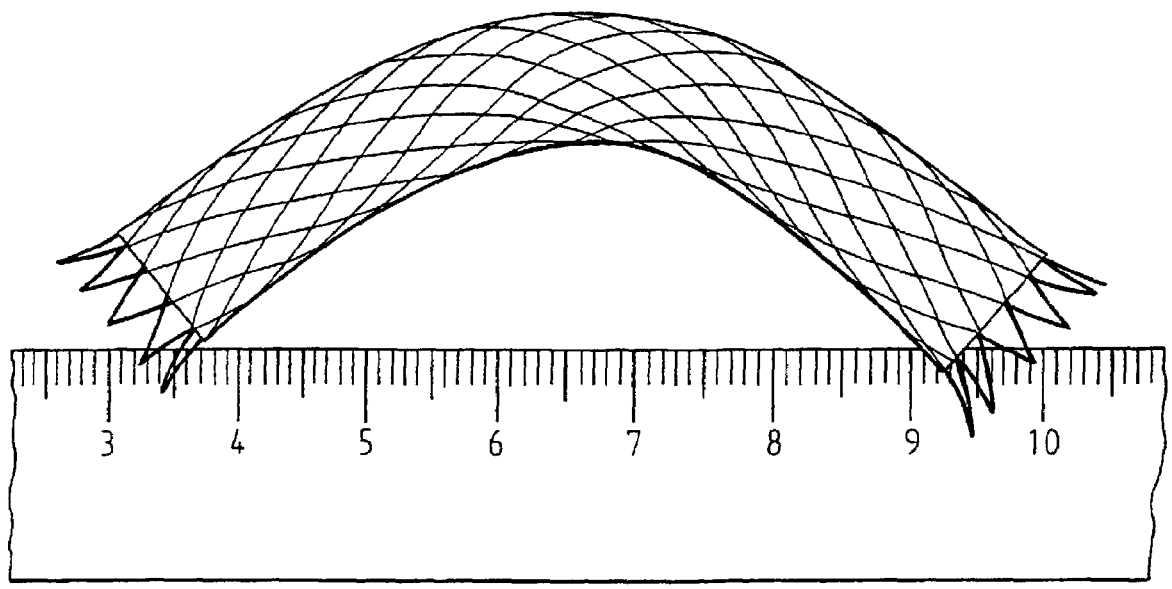
FIG. 7 is a picture of a fully encapsulated stent being tested for flexibility.
Figure 8:
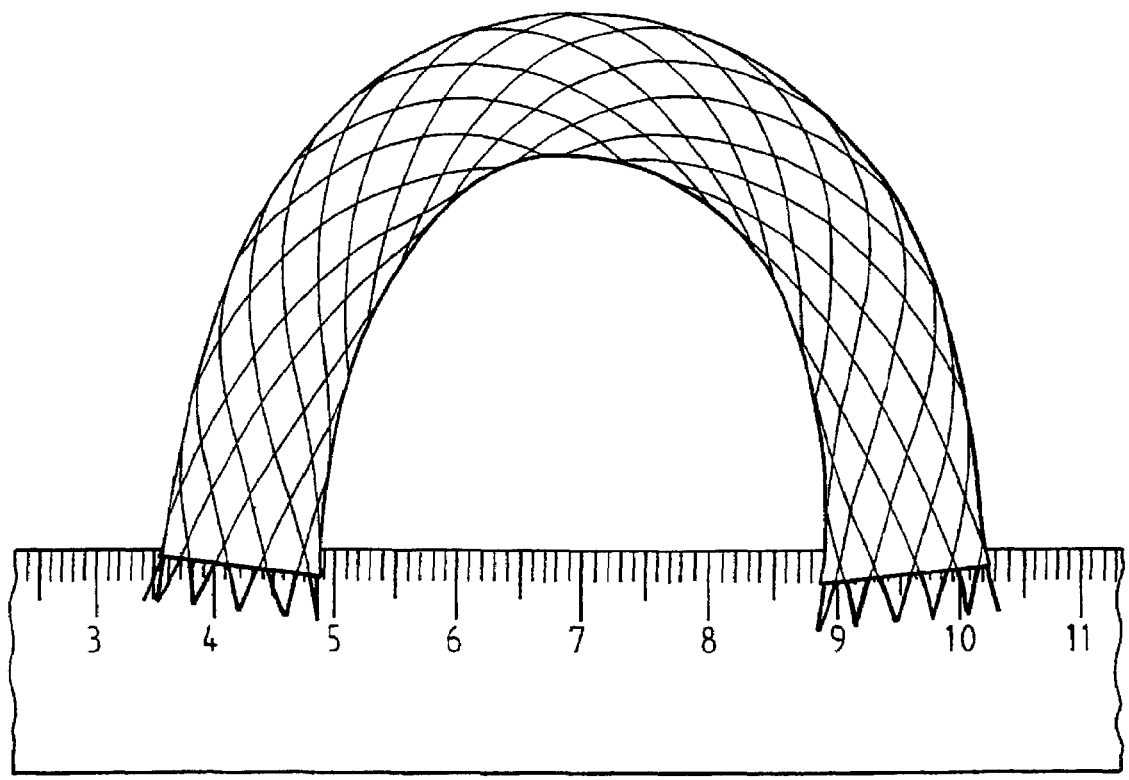
FIG. 8 is a picture of the FIG. 1 graft being tested for flexibility in the same manner as FIG. 7.

FIGS. 2 and 3 illustrate cross-sections of FIG. 1. A cross-section of stent-graft 10 is taken along line 2-2, through an end 22 of the device 10 in FIG. 2 and long line 3-3 through the mid-section 24 in FIG. 3. These two cross-sections are shown to illustrate the additional layer of ePTFE 30 that is present on the luminal surface of the end 22 and not present on the luminal surface of the mid-section 24. As mentioned, the reason for encapsulating only the ends 22 of stent-graft 10 is to increase its flexibility over a fully encapsulated stent, thereby allowing it to be bent into extreme curves without kinking. Most of the length of the device is covered by only a single layer of ePTFE which is extremely flexible and which does not strongly interact with the stent. Therefore, the flexibility of the single layer area is essentially that of the underlying stent device. FIG. 7 shows a fully encapsulated shape memory alloy stent bent in essentially as sharp a curve as possible. Note that the covering material is showing kinks or distortions due to the inability of the covering material to move longitudinally relative to the stent structural members. FIG. 8 shows an identical shape memory alloy stent covered according to the present teaching. Only zones towards each end of the device are fully encapsulated. Note that the device is capable of being bent into a much sharper curve with little or no distortion of the covering or the underlying stent.

An additional advantage is that the force necessary to deploy the stent-graft 10 using a coaxial deployment system ought to be less than for a fully encapsulated stent. This is due to the reduction in the thickness of covering material. Furthermore, by reducing the amount of covering material, the overall profile of the deployment system is reduced, allowing a wider range of applications. Another advantage enjoyed is ease of manufacture compared to stent-graft devices that place multiple stent rings over ePTFE tubing. Finally, an advantage over stent-grafts with a single layer of biocompatible material over the entire graft length is that, because a strong bond is created in the encapsulated region, it is possible to transmit a pulling force from one end of the stent of the present invention to the other via the covering, making it possible to load into a sheath using pulling techniques. The preferred bare stent designs (chosen for flexibility and low profile) do not permit transmission of a pulling force in a longitudinal axial direction. This is because flexibility is increased and profile reduced by removing connections between longitudinally neighbouring struts. The limited number of longitudinal connections has inadequate tensile strength to transmit the pulling force without failure. In the case of a true single layer covering (without use of adhesive, etc.) pulling on the covering causes the covering to slip off the stent. In the case of sutured single layer device pulling on the covering may cause the suture holes to enlarge and even tear.

Figure 4:
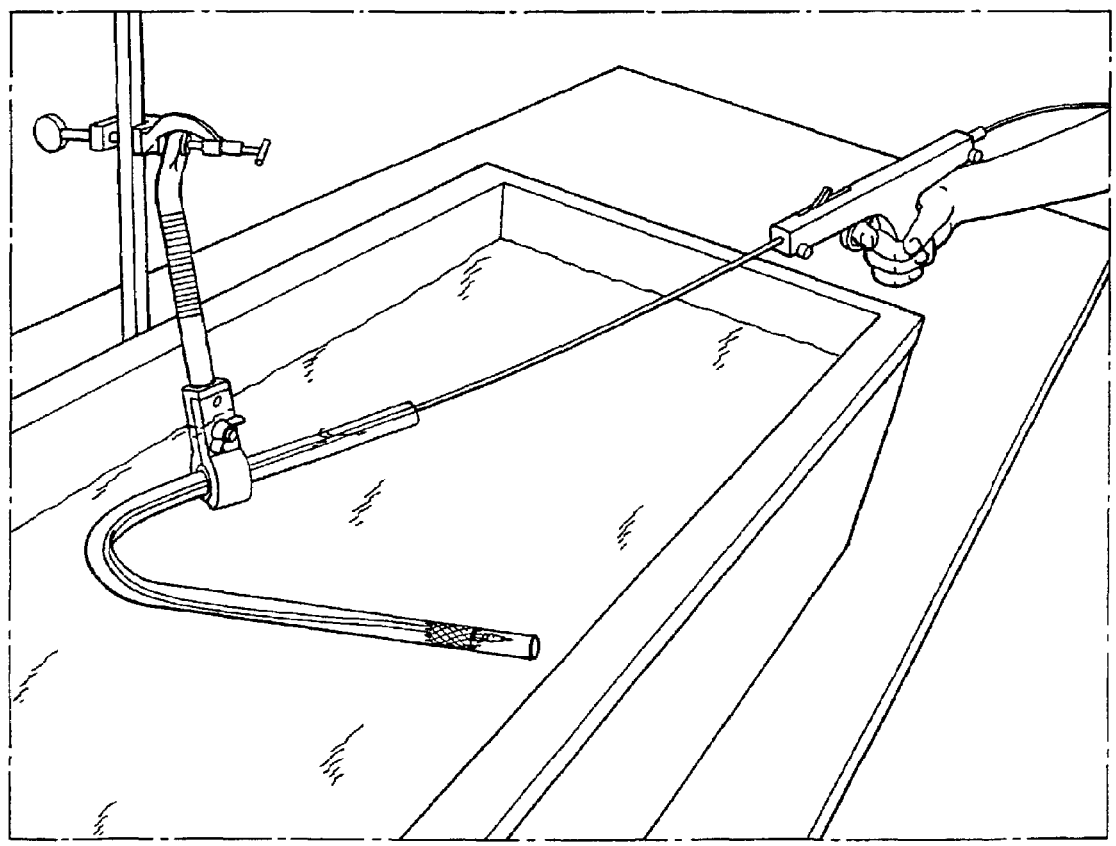
FIG. 4 is an overview picture of the deployment of the graft.
Figure 5:
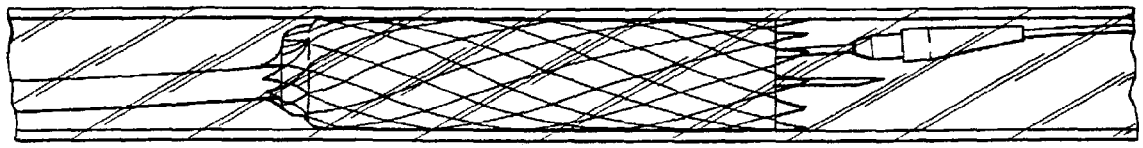
FIG. 5 is a close-up view of the device being partially deployed.
Figure 6:
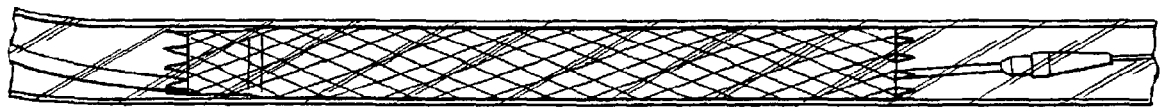
FIG. 6 is a close-up view of the device fully deployed.

In the case of a biliary stent an especially tortuous delivery path must be used. There are two main techniques for such delivery. If the stent is delivered transhepatically, it is inserted through percutaneous vasculature, through the bulk of the liver and down the hepatic duct where it must make a bend of around 45 degrees between the hepatic and the bile duct. If the stent is delivered endoscopically it enters the bile duct via the papilla and must pass through multiple bends, the most severe of which is about 90 degrees with a 10 mm radius. Clearly, an extremely flexible stent is required. To further illustrate the deployment of the prototypes, FIGS. 4-6 have been provided. FIG. 4 shows an overview of the prototypes being deployed into a glass model of a bile duct using a pistol handgrip delivery system. Note the bend that the stent must navigate. FIG. 5 shows a close-up view of a prototype, as it is partially deployed from the sheath. FIG. 6 shows a close-up view of a fully deployed prototype.

The "Flexx" stent used in these experiments is a specially designed stent configured for enhanced flexibility. Stents of this type are cut from tubes of Nitinol shape memory alloy and then expanded on a mandrel. The size memory of the device is set on the expanded form. The device is then compressed to the appropriate dimensions of the original tube for insertion into a patient. Once properly located in the patient, the device is released and can self-expand to the "memorized" expanded dimension. Although the entire device is a single unitary piece as shown in FIG. 9 in its expanded state, this design conceptually comprises a plurality of zigzag hoops 64 joined by longitudinal joining points 62.

FIG. 10 shows the cut device prior to expansion, to illustrate that each zigzag hoop 64 is attached to each adjacent zigzag hoop 64 (FIG. 9) by only a pair of joining points 62. Note the opening regions 60 between the joining points 62. It will be apparent that such a structure affords considerable lateral flexibility to the entire compressed structure. If there were a larger number of joining points 62, lateral flexibility of the compressed device would be impeded. On the other hand, the very open structure of the expanded stent (FIG.9) offers little resistance to tissue infiltration.

These two factors account for the unusual suitability of The Flexx design. The use of a covering of ePTFE or other biocompatable material prevents tissue infiltration despite the very open nature of the Flexx design. The use of end encapsulation (as oppose to encapsulation over the entire length of the device) preserves most of only a single layer of covering over much of the stent results in a low profile in the compressed configuration so that the device can be inserted through small bile ducts and other retricted vessels. The use of only a very limited number of joining points 62 provides the lateral flexibility required for insertion through tortuous bile ducts and other similarly twisted vessels.

Figure 11:
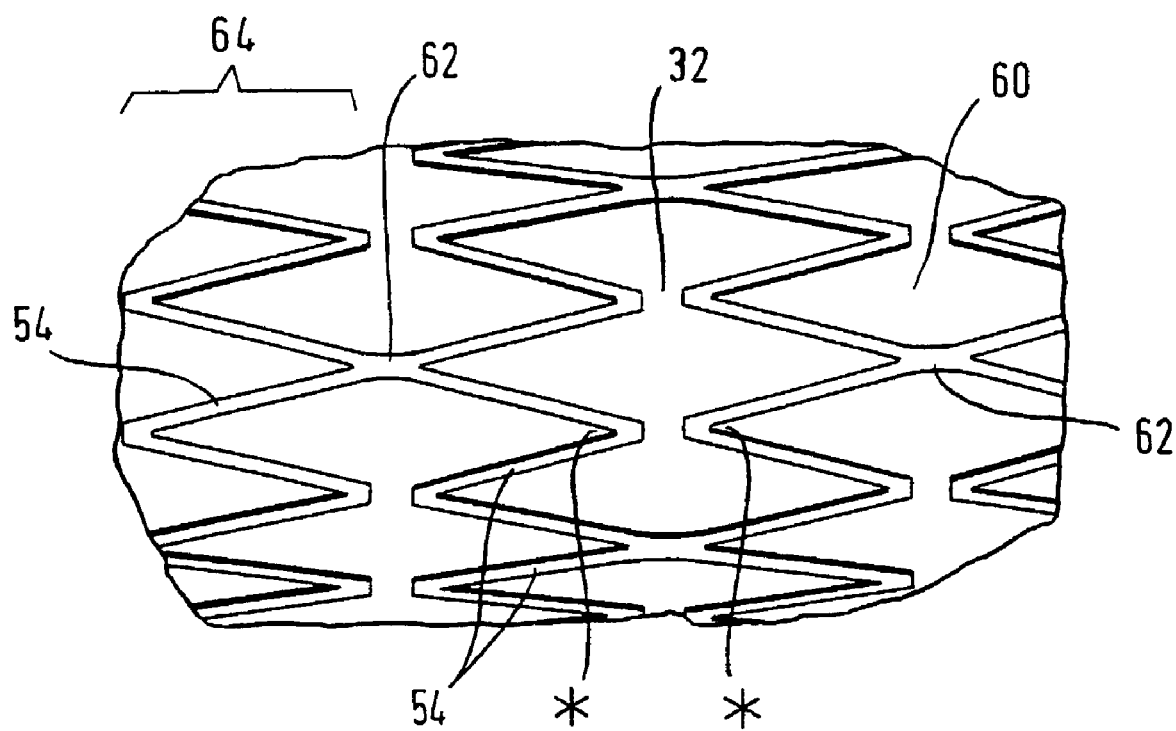
FIG. 11 shows a close-up of the strut structure of the expanded stent of FIG. 9.

FIG. 11 is a close-up of a portion of FIG. 9 and shows the adjacent zigzag hoops 64 and the joining points 62. Each hoop 64 is formed from a zigzag pattern of struts 54. These struts have the thickness of the Nitinol tube from which the device is laser cut with a width, in this embodiment, of about 0.2 mm. There is a joining point 62 between a given hoop 64 and an adjacent hoop 64 every third strut 54 with the joining points 62 alternating from the left-hand adjacent to the right-hand adjacent hoop 64 so that six struts 54 separate the joining points 62 between any two hoops 64. Gaps 32 replace the joining points 62 where the intersections of zigzag hoops are not joined.

Figure 12:
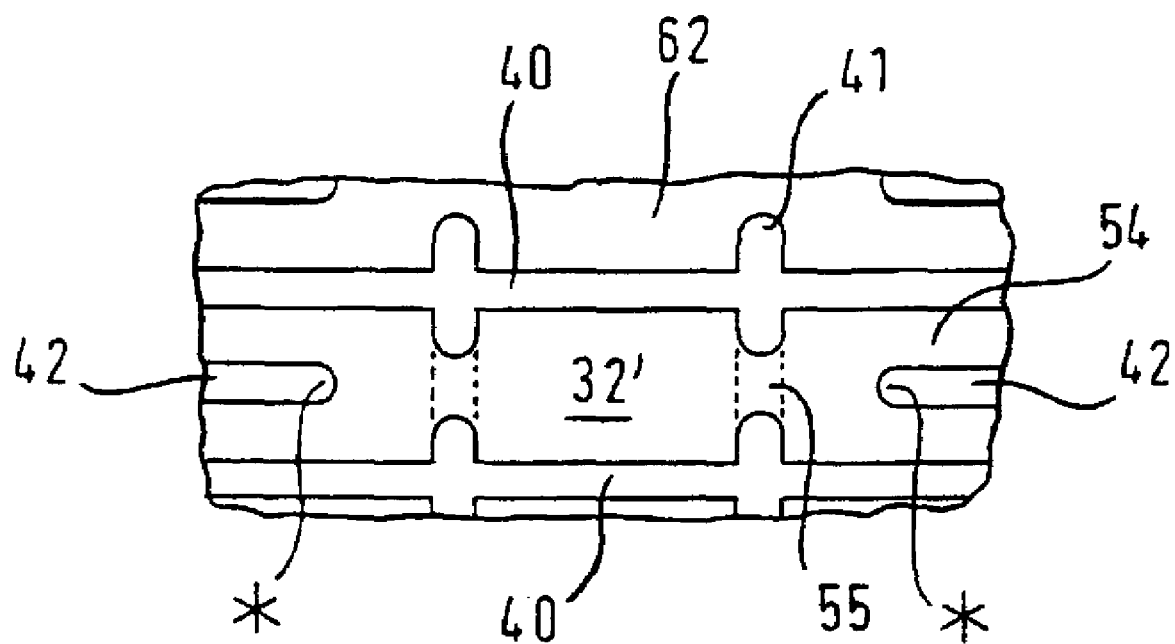
FIG. 12 shows a close-up view of the flexible stent design of FIG. 9 immediately after being cut from a metal tube and before being expanded into the form of FIG. 11.

FIG. 12 shows a close-up of the non-expanded cut structure of FIG. 10. Cuts 40, 41, and 42 are regions where the metal has been vaporized by a computer-controlled cutting laser. The cut 40 between blind cuts 41 will expand to form the window 60. Cut 42 forms the intersection point ★ of the struts 54, which show portions of two ring stents 64. Partially cut regions 55 define a scrap piece of metal 32', which is removed following expansion to form the gaps 32. In FIG. 12 the partially shown region about the cut 40, and above the scrap piece 32', is a joining point 62. Because a structure with only two joining points 62 between adjacent hoops 64 is too fragile to withstand the tensile stresses endwise on the stent cylinder which are liable to be encountered in the expansion as from FIG. 12 to FIG. 11,the pieces 32' act as reinforcing joining points for the radial expansion process and are not cut out as scrap until afterwards. Following expansion, the scrap pieces 32' are removed to form the gaps 32. This structure can be deformed into the reduced diameter flexible structure. It will be apparent that although this structure is described and pictured as having circumferential hoops 64, the hoops can also be arranged in a helical manner to achieve the objects of the improved design.

FIG. 13 shows one end portion of the FIG. 9 stent, again with struts 54. The end zone E is characterised by a rigidity rather more than that of the central cylindrical zone of the stent, by virtue of an absence of cuts and windows 60, as can be perceived in the FIG. 10 drawing. At the end vertex 70 of each cell 72 in the first circumferential ring of cells of the stent, the material of the stent matrix is continued into an extending portion 74 (FIG. 14) with a width comparable to its thickness dimension so that, in cross-section, it is more or less square. On each such square section spigot 74 is mounted a spherical Nitinol bead 76 which has a through bore on a diameter of the bead, to receive the spigot 74. The Nitinol bead 76 is welded to the spigot 74. It will be appreciated that, by virtue of the rounded surface and greater thickness of the sphere 76 relative to the struts 54, the free vertices defining the end of the stent, and the end of each cell 72 in the end ring of cells of the stent, is less likely to cause trauma in the bodily tissue in which the end vertices 70 is embedded, than if the spigot 74 and spheres 76 were absent.

Furthermore, as shown in FIG. 16, the ring of beads 76 brings advantages when it comes to loading the stent onto a delivery system, and keeping control of the stent while the stent is being deployed into the body from the delivery system. Specifically, the ring of relatively thick beads 76 provides a point of purchase for gripping surfaces to impose forces on the stent, while it is being loaded into a delivery system, and while it is being deployed from that delivery system. In one example, the beads 76 could be gripped between circumferential surfaces, one inside the stent annulus and one outside the stent annulus, with a spacing between such co-axial surfaces which is wide enough to receive the thickness of the stent matrix, but does grip the spheres 76 on each side of the thickness of the stent matrix.

It has been described above how the form of stent covering allows the stent to be subjected to axially directed pulling forces, even while the centre section of the stent is extremely flexible. It is to be noted that, in the present application, the flared end sections of the stent need not be so flexible, and are not made so flexible, and are therefore better adapted to carry axial pulling forces. In the centre section of the stent, where the enhanced flexibility renders the stent less able to tolerate axial pulling forces, the forces can be shared with the stent covering. Thus, with the illustrated embodiment, substantial pulling forces can be applied to the ring of beads 76 on one end of the stent, with the stent construction able to transmit such pulling forces all the way to the other end of the stent. It is a significant advantage to be able to maintain full control of the movement of the stent, all from one extreme end of the stent. Note also that the friction-reducing properties of PTFE, and the presence of an abluminal PTFE sleeve over most of the length of the stent, will facilitate loading of the stent into a delivery system, and deployment of that stent from the delivery system, all under the control of a grip on the stent which is applied only at one extreme end of the stent length.

The ring of beads 76 at each end of the stent allows accurate radioscopic tracking of the stent from outside the body.

FIG. 14 shows in more detail the mounting of a bead 76 on a spigot 74 of the stent matrix. The bead 76 has a through bore 80, made by laser drilling, which has the rectangular cross-section visible in FIG. 15, to accommodate relatively snugly the rectangular cross-section 82 of the spigot 74. To secure the bead 76 to the spigot 74, laser radiation is used to create a welding bead 82 at the tip of the spigot 74. The stent matrix, the spigot 74, the bead 76 and the weld bead 82, are all of nickel titanium alloy.

Moving now to FIGS. 16 and 17, the stent 12 is shown schematically within the truncated cone of a loading mandrel 90, with its leading end at the narrow end of the cone, tipped by the beads 76. Within the leading end of the stent is a loading rod 92 with a somewhat larger diameter head 94, the transition from the head 94 to the cylindrical portion 96 of the rod 92 is accomplished by an arcuate shoulder surface 98. The concave outer surface of the shoulder 98 has a curvature which corresponds to the curvature of the beads 76.

Beyond the narrow end of the truncated cone 90 is a gripping sleeve 100 which has at its gripping end 102 an arcuate gripping shoulder 104, also having a curvature corresponding to that of the spherical surface of the bead 76.

As can be seen from FIG. 17, drawing the gripping rod 92 down on to the beads 76 achieves an entrapment of the beads 76 in an annulus defined by the gripping shoulders 98 and 104. With the position of the gripping rod 92 maintained close to the gripping end 102 of the gripping sleeve 100, further pulling down of the gripping rod 92, away from the truncated cone 90 permits the advancement of the stent 12 into the cylindrical space shown in FIG. 17, within the block 106.

The block 106 receives a sleeve 108 in which the stent 12 is to be housed, in a delivery system for placing the stent 12 at a desired location within the body, for location, a catheter. Continued downward pulling on the gripper rod 92, beyond the position shown in FIG. 17, can carry the stent 12 fully inside the sleeve 108 of the catheter delivery system. Once the stent 12 is within the sleeve, the gripping sleeve 100 can be withdrawn forwardly, i.e. downwardly in the FIG. 17 view, while the gripper rod 92 can be withdrawn rearwardly from the stent, i.e. upwardly as shown in FIG. 17. Alternatively, once the gripping sleeve 100 is withdrawn, it may be possible to withdraw the gripper rod 92 also forwardly, given a degree of resilience in the sleeve 108 to allow the enlarged head 94 to slide past the beads 76.

A variant is shown in FIG. 18. A bead 76 has a through bore 80 which receives a spigot 74 defined by two parallel resilient fingers 76a, 76b formed out of the stent matrix. Each finger has a tip 76c and each tip has a re-entrant surface 76d which abut the outer surface of the bead 76 when the tips emerge from the bore 80, to resist reverse movement of the fingers in the bore 80.

EXAMPLE

An esophageal stent graft was constructed from a Nitinol cylinder 0.3 mm thick. A laser controlled by a computer was used to cut a multiplicity of staggered cuts in the cylinder wall, parallel to the cylinder length, to create struts having a width of 0.167 mm. Cuts perpendicular to the length were also made in a mid-length portion of the tube length, for selective removal of scrap struts to enhance the flexibility of the mid-length section.

On a mandrel the tube is brought to its pre-set expanded configuration. The end portions of the expanded stent matrix cylinder were further expanded by the introduction of a tapered annulus between the stent matrix and the cylinder, one at each end of the stent. The stent matrix, on its mandrel, was then heated in an oven to "set" the configuration to be "remembered" by the shape memory alloy. Then, the scrap struts 32' were removed.

Following such heat-setting, the matrix was removed from the mandrel and a Nitinol bead, with preformed diametral rectangular bore, as shown in FIG. 15, was laser-welded to each spigot (FIG. 14, reference 74) present at each end of the stent matrix, to provide 18 beads at each end of the stent. On a fresh mandrel, the beaded stent matrix was then subjected to further polishing. On a sintering mandrel, two bands of ePTFE tape were wrapped, at spaced locations corresponding to each end of the cylindrical middle section of the stent matrix. The polished matrix was then mounted on the mandrel, overlying the PTFE bands. Then PTFE tape was wrapped around the stent matrix, to cover the entire cylindrical mid-section of the stent. Then the wrapped matrix, on its mandrel, was heated in an oven to sinter the PTFE and bond the two PTFE luminal bands to the abluminal PTFE sleeve, through the apertures of the stent matrix. The stent matrix was then ready for loading into a delivery system, as explained in relation to drawing FIGS. 16 and 17.

For this esophageal stent, beads of diameter 0.95 mm were used. The number of longitudinal slits around the circumference of the stent cylinder was 36. The length of each flared transition section, adjacent to the mid-section of the stent cylinder, was 8 mm. In the expanded configuration, the outside diameter of the stent matrix in the mid-section of its length was 20 mm. The "crown" ring of beads at each end had a diameter of 28 mm. The angle of the flared section linking the cylindrical mid-section to the expanded "crown" ends was 15 degrees. Each expanded crown end section had a length of 20 mm. The wall thickness of the Nitinol tube which is the basis of the stent matrix was 0.3 mm.

Those skilled in the art will readily appreciate, from the above description, further advantageous technical effects arising from the technical features of the invention described above. While the application of the invention to an oesophageal stent graft takes particular advantage of the technical features described above, they are also of substantial interest in other applications of stents.

The invention claimed is:

1. An elongate, tubular, longitudinally extending stent matrix which defines and surrounds a longitudinal flow path, the matrix being capable of expansion during deployment in a body lumen, from a small diameter delivery configuration to a large diameter lumen wall-supporting configuration, the matrix comprising:

a multiplicity of cells formed from a plurality of struts, at least two of the plurality of cell-forming struts intersecting to define a unitary vertex;

at least one mounting portion extending longitudinally from the vertex;

a bead fixed to the at least one mounting portion, said bead having a longitudinally extending aperture which receives the at least one mounting portion, said bead is fixed to the matrix by a mechanical engagement of co-operating surfaces, the co-operating surfaces are disposed on the at least one mounting portion and are resilient and wherein the aperture of the bead defines a female receiving portion, and the resilient co-operating surfaces are fingers having tips, the fingers lying in the closed loop and elastically deformable to bring the tips of the fingers closer together, to advance into the female receiving portion of the bead.

2. A matrix as claimed in claim 1 wherein the at least one mounting portion is arranged as an anchor to resist movement of the matrix relative to the tissue of said body lumen.

3. A matrix as claimed in claim 1, wherein the at least one mounting portion extends longitudinally from the vertex to define a spigot having at least two parallel sides.

4. A matrix as claimed in claim 1, created out of sheet material.

5. A matrix as claimed in claim 4 wherein the sheet material is a seamless tube.

6. A matrix as claimed in claim 4 wherein the sheet material is initially flat, then formed into a tube.

7. A matrix as claimed in claim 1 which is a self-expanding stent matrix.

8. A matrix as claimed in claim 7 wherein the material of the matrix is a shape memory alloy.

9. A matrix as claimed claim 1 which is a non-self-expansible stent, which undergoes plastic deformation on expansion.

10. A matrix as claimed in claim 9 wherein the material of the matrix is stainless steel.

11. A matrix as claimed in claim 1 wherein the material of the bead has an electrochemical potential which is the same or substantially the same as that at the matrix material.

12. A matrix as claimed in claim 11 wherein the material of the bead and the material of the matrix is the same.

13. A matrix as claimed in claim 11 wherein the bead is fixed to the matrix by welding.

14. A matrix as claimed in claim 1 wherein the aperture of the bead is a through bore, and the fingers are long enough to extend through the bore until the tips extend out of the end of the bore.

15. A matrix as claimed in claim 14 wherein the finger tips have a re-entrant surface to resist reverse movement of the finger tips into the bore.

16. A matrix as claimed in claim 1 wherein the bead is fixed to the matrix by an intervening tie-layer of adhesive.

17. The stent matrix of claim 1, further comprising opposing ends, at least one of the ends being contiguous with at least one hoop of cell-forming struts, the vertex being located in the at least one hoop.

18. A matrix as claimed in claim 17, wherein the at least one mounting portion comprises a plurality of mounting portions spaced at circumferentially spaced intervals along said at least one hoop.

19. A matrix as claimed in claim 18 wherein the plurality of mounting portions comprise a bead is fixed to every said mounting portion in said at least one hoop.

20. A matrix as claimed in claim 19 wherein all the beads in the at least one hoop have the same form.

21. A matrix as claimed in claim 19, and exhibiting a hoop of beads at the opposite end of the matrix from said at least one hoop.

22. A matrix as claimed in claim 18 wherein the plurality of mounting portions comprise a bead fixed to every other said mounting portion in said at least one hoop.

23. A matrix as claimed in claim 22 wherein all the beads in the at least one hoop have the same form.

24. A matrix as claimed in claim 22, and exhibiting a hoop of beads at the opposite end of the matrix from said at least one hoop.

25. A matrix as claimed in claim 18 wherein the plurality of mounting portions comprise a plurality of beads, each of the plurality of beads fixed to a different one of said plurality of mounting portions, each of the plurality of beads in the at least one hoop have the same form.

26. A matrix as claimed in claim 25 wherein the arrangement of mounting portions and beads are the same at opposite ends of the stent matrix.

27. A matrix as claimed in claim 17 wherein the at least one hoop is flared to define a diameter, when expanded, that is greater than a longitudinally adjacent hoop of cell forming struts.

28. A stent as claimed in claim 1 which includes a covering of at least a portion of the matrix.

29. 33. stent as claimed in claim 28 wherein said portion includes a mid-length portion of the matrix and excludes end portions of the matrix.

30. A stent as claimed in claim 28 wherein the matrix has opposite ends a diameter between opposite ends which, at its large diameter configuration, is smaller than the diameter of at least one end portion of the matrix.

31. A stent as claimed in claim 30, having in its large diameter configuration three distinct diameter zones, namely,
   (1) a mid-length more or less constant diameter,
   (2) an end zone at each end of the matrix, each end zone having a more or less constant diameter greater than said mid-length zone; and
   (3) a transition zone of changing diameter, steplessly joining the mid-length zone to each end zone.

32. An elongate, tubular, longitudinally extending stent matrix which defines and surrounds a longitudinal flow path, the matrix being capable of expansion during deployment in a body lumen, from a small diameter delivery configuration to a large diameter lumen wall-supporting configuration, the matrix comprising:
   a multiplicity of cells formed from a plurality of struts, at least two of the plurality of cell-forming struts intersecting to define a unitary vertex;
   at least one mounting portion extending longitudinally from the vertex;
   a bead fixed to the at least one mounting portion, said bead having a longitudinally extending aperture which receives the at least one mounting portion,
   wherein the bead is spherical.

33. A matrix as claimed in claim 32 wherein the bead is fixed to the matrix by a mechanical engagement of co-operating surfaces.

34. A matrix as claimed in claim 33 wherein the co-operating surfaces are disposed on the at least one mounting portion and are resilient.

* * * * *